United States Patent [19]

Hellman, Jr.

[11] Patent Number: 4,800,010

[45] Date of Patent: Jan. 24, 1989

[54] LOCKABLE, ROTATING ELECTROPHORESIS DEVICE

[75] Inventor: Robert R. Hellman, Jr., Southbury, Conn.

[73] Assignee: Eastman Kodak Company, Rochester, N.Y.

[21] Appl. No.: 187,117

[22] Filed: Apr. 28, 1988

[51] Int. Cl.$^4$ ............................................. G01N 27/26
[52] U.S. Cl. ............................ 204/299 R; 204/182.8;
74/527; 74/531; 188/69; 188/71.1
[58] Field of Search ............. 204/299 R, 182.8, 182.9, 204/180.1

[56] References Cited

U.S. PATENT DOCUMENTS

| | | | |
|---|---|---|---|
| 3,436,983 | 4/1969 | Krantz | 74/527 |
| 3,704,353 | 11/1972 | Halla | 200/153 J |
| 4,290,871 | 9/1981 | Hoefer et al. | 182/8 |
| 4,292,161 | 9/1981 | Hoefer et al. | 182/8 X |

Primary Examiner—John F. Niebling
Assistant Examiner—John S. Starsiak, Jr.
Attorney, Agent, or Firm—Dana M. Schmidt

[57] ABSTRACT

There is disclosed a releasable locking mechanism for holding a rotating device in place. The mechanism is particularly adapted for use with an electrophoresis device comprising a support for mounting at least one gel plate assembly in a generally vertical orientation, a pair of buffer tanks for each gel plate assembly, means for mounting the pair of tanks at opposite ends of each gel plate assembly, and means for applying a current at the opposite ends of each plate assembly.

The locking mechanism preferably features a two-position push latch and either a lock plate provided with teeth or a disk brake, the latch being positioned to directly or indirectly cause engagement of the teeth of the plate or brake when in one of its two positions.

8 Claims, 12 Drawing Sheets

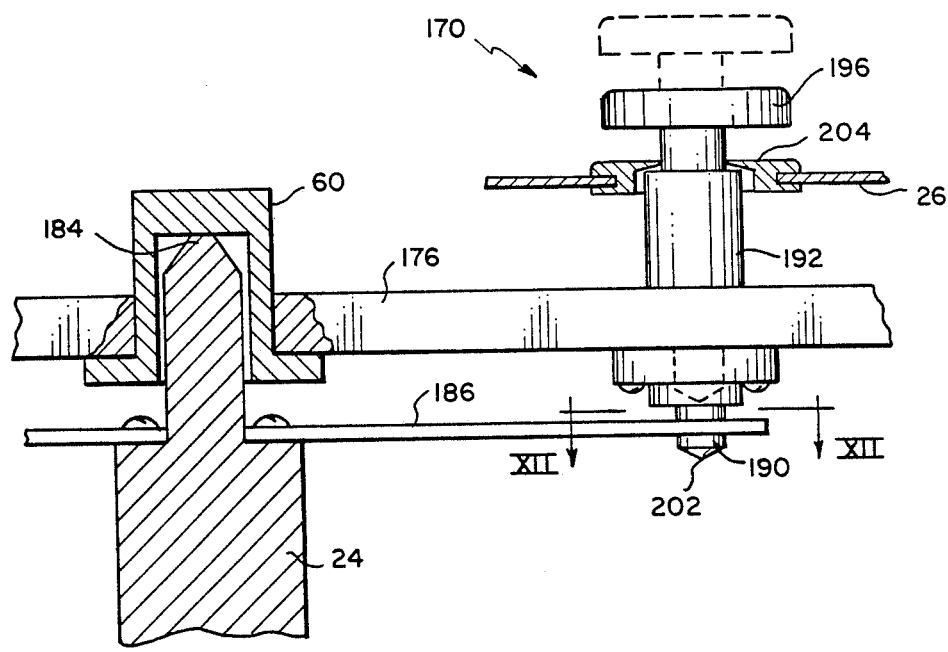
FIG. 11
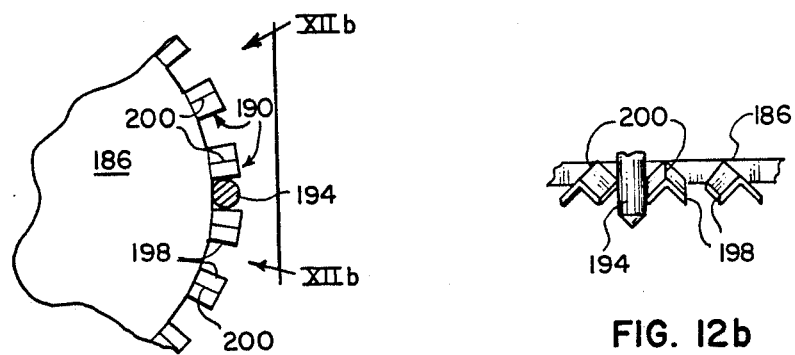
FIG. 12a
FIG. 12b

LOCKABLE, ROTATING ELECTROPHORESIS DEVICE

FIELD OF THE INVENTION

This invention relates to an electrophoresis device, particularly one that provides for at least two separate gel plate assemblies on the same device.

BACKGROUND OF THE INVENTION

Double-sided electrophoresis devices have been provided in the past, wherein two gel plate assemblies are mounted substantially vertically. The operator must get at each plate separately, from the front, to load samples and inspect results. Heretofore, such double-sided units have been awkward to use, because they have not been easily turned to allow access to the "other" side. That is, either the entire unit has to be picked up, or the operator walks around the unit to the other side. Picking up the entire unit is not feasible, since it is not sufficiently small or light-weight to render this a simple operation. Furthermore, the device is full of liquids, even harmful liquids, that can be spilled, so that picking it up is a serious hazard.

Therefore, prior to this invention there has been a substantial need to make an electrophoresis device, particularly those mounting more than one gel plate, to be more readily accessible from several sides. Mere rotatability has not been adequate, since typically the comb of the gel plate assembly has to be carefully removed and reinserted after gel set, to provide cavities for sample introduction. Such a maneuver cannot be done easily on a device that is freely rotatable.

SUMMARY OF THE INVENTION

The above-mentioned problems of the prior art constructions have been solved with a construction that provides a support for gel plate assemblies that is both rotatable and temporarily lockable.

More specifically, there is provided a releasable locking mechanism for a device rotatably mounted on a base, the device including a support and a base on which the support is rotatably mounted. In accord with one aspect of the invention, the locking mechanism comprises a lock plate secured to the base, the plate comprising a plurality of teeth extending around the circumference of the plate, and means on the support for engaging the plate between any two adjacent teeth, the engaging means being directly or indirectly activatable by a two-position push latch on the support having a downwardly extending member, the member being latchable in two positions, one of the positions being effective to place the engaging means between two teeth, and the other of the positions being effective to remove the engaging means from all of the teeth of the lock plate.

In accord with another aspect of the invention, the locking mechanism comprises a disk brake secured to the base, and means on the support for engaging the brake, the engaging means including at least one brake pad, and further including a two-position push latch on the support having a downwardly extending member that is latchable in two positions, the engaging means being activatable by the latch member on the support, one of the positions of the latch member being effective to push the brake pad against the disk brake, and the other of the positions being effective to remove the pad from the disk brake.

In accord with yet another aspect of the invention, there is provided an electrophoresis device for electrophoretically separating charged compounds, the device comprising a support for mounting at least one gel plate assembly, a pair of buffer tanks for each gel plate assembly, means for mounting the pair of tanks at opposite ends of each gel plate assembly, and means for applying a current at the opposite ends of each plate assembly. The device is improved in that it further includes a base on which the support is mounted, means for rotating the support about the base about a generally vertical axis, and means for releasably locking the support in at least one position relative to the base.

Thus, it is an advantageous feature of the invention that a liquid-containing, multi-sided device, such as an electrophoresis device, can be rotated and releasably locked in a desired position, without having to pick up and rotate the entire device.

It is another advantageous feature of the device that it is either locked against rotation or freely rotating, with only one step required to switch from one to the other.

Other advantageous features will become apparent upon reference to the following "Detailed Description", when read in light of the attached drawings.

BRIEF DESCRIPTION OF THE DRAWINGS

FIG. 11 is a fragmentary elevational view, partly in section, of the frame shown in FIG. 2, illustrating the details of the locking mechanism;

FIG. 12a is a fragmentary sectional view taken along the line XII—XII of FIG. 11;

FIG. 12b is a fragmentary sectional view taken generally along the line XIIb—XIIb of FIG. 12a;

DESCRIPTION OF THE PREFERRED EMBODIMENTS

In the following discussion, the releasable locking invention is described particularly as it applies to a rotatable two-sided electrophoresis device, its preferred usage. In addition, it is applicable to any device rotatably mounted on a base, which requires releasable locking in a desired position. It is also applicable to an electrophoresis, or any other device, having more than two sides requiring access.

Features of the electrophoresis device also described herein, other than the releasable, locking mechanism used with the rotatable mounting include subject matter that is separately claimed in the following commonly owned related applications co-filed with this application by me: "Improved Electrophoresis Device With Near-Vertical Gel Plates" bearing Ser. No. 07/187,670; "Improved Gel Plate Assembly for Electrophoresis" bearing Ser. No. 07/187,668; and "Electrophoresis Device With Removable Buffer Tank" bearing Ser. No. 07/187,152.

Parts described herein as being "vertical", "horizontal", "up", "bottom", or with similar direction terms, refer to their orientation when in their normal use.

Figure 1:
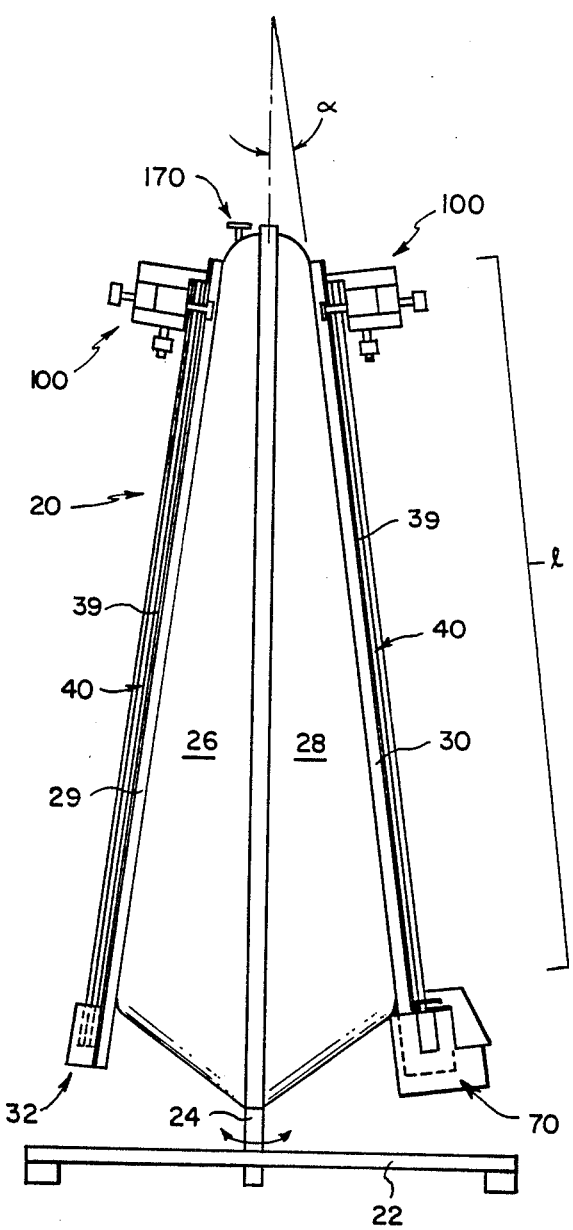
FIG. 1 is an elevational view of an electrophoresis device incorporating the features of the invention.
Figure 2:
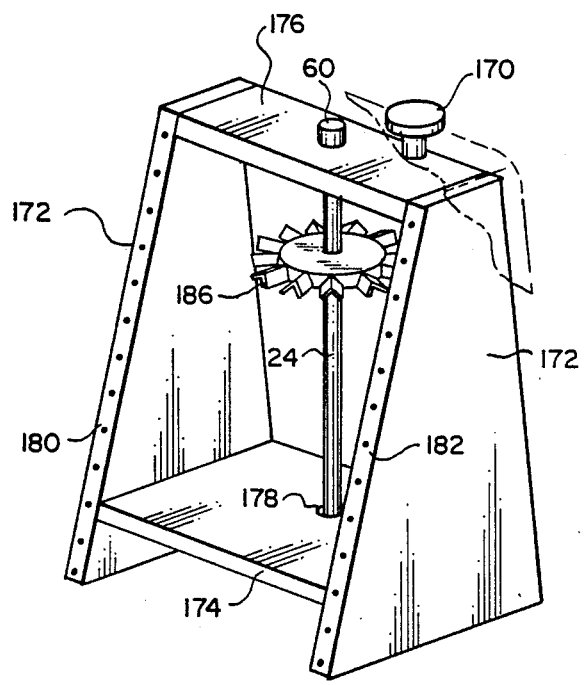
FIG. 2 is a fragmentary isometric view of the interior of the device, partly illustrating the rotatability and lockability of the device.
Figure 3:
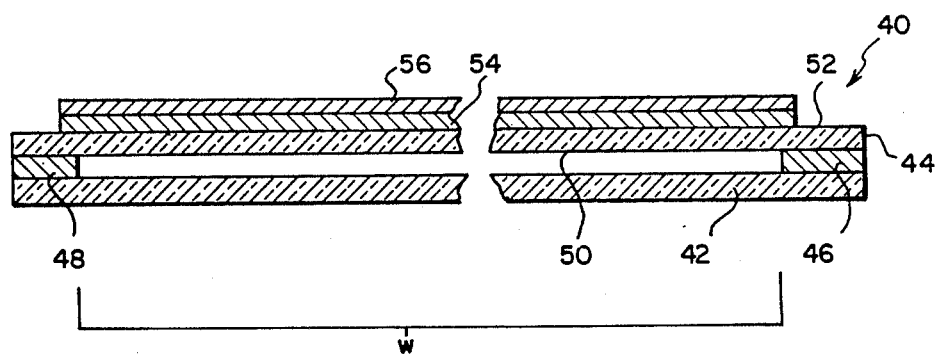
FIG. 3 is a fragmentary sectional view of the gel plate assembly.

An electrophoresis device 20 constructed in accordance with the invention comprises, FIG. 1, a support generally comprising a base 22, a vertical post 24, two clam shell bodies 26, 28 mounted on either side of post 24, and supporting rails 29, 30 providing a support surface for a gel plate 40 that is more completely shown in FIG. 3. Shell bodies 26 and 28 are mounted for rotation, FIG. 2, on post 24, by reason ob bushing 60 that rides on the point of post 24. A locking mechanism 170 is provided, effective to releasably hold shells 26, 28 against further rotation. A pair of buffer tanks 70 and 100 are mounted at the bottom of device 20, FIG. 1, and top, respectively, as is conventional. (Only one bottom buffer tank 70 as shown in FIG. 1 for clarity, to allow illustration of trough 32.)

Figure 4:
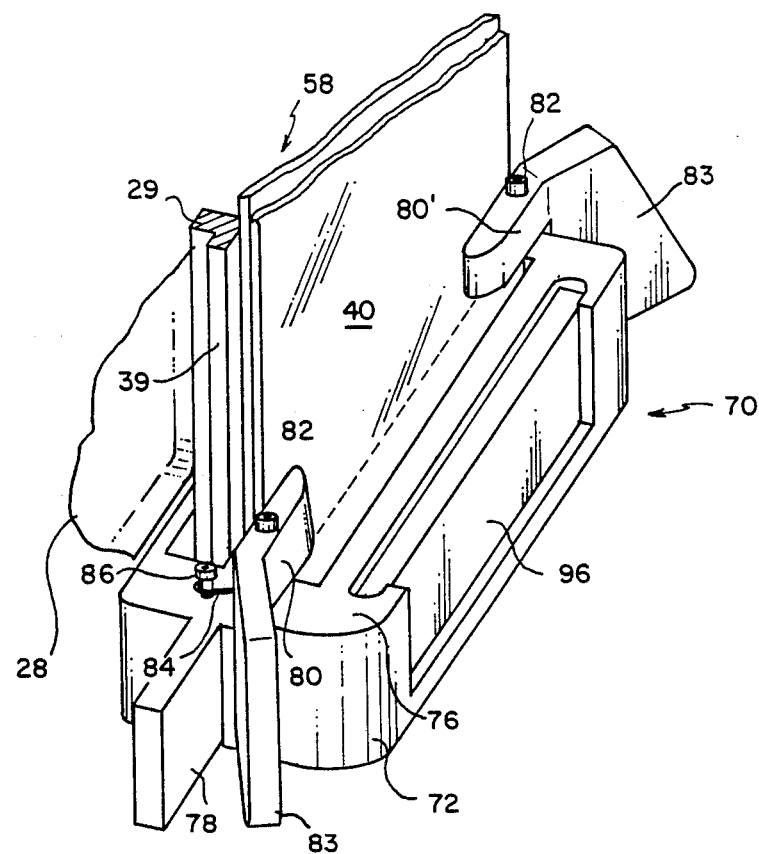
FIG. 4 is a fragmentary isometric view of the bottom buffer tank of the device.
Figure 5:
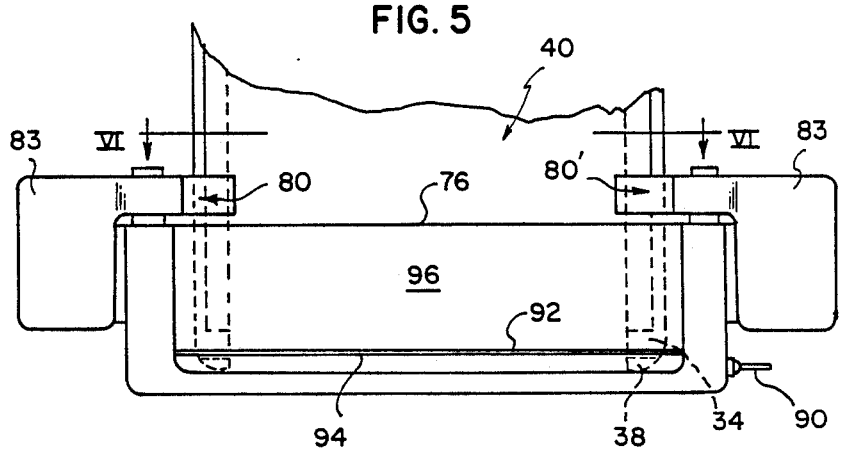
FIG. 5 is a fragmentary front elevational view of the tank of FIG. 4.
Figure 6:
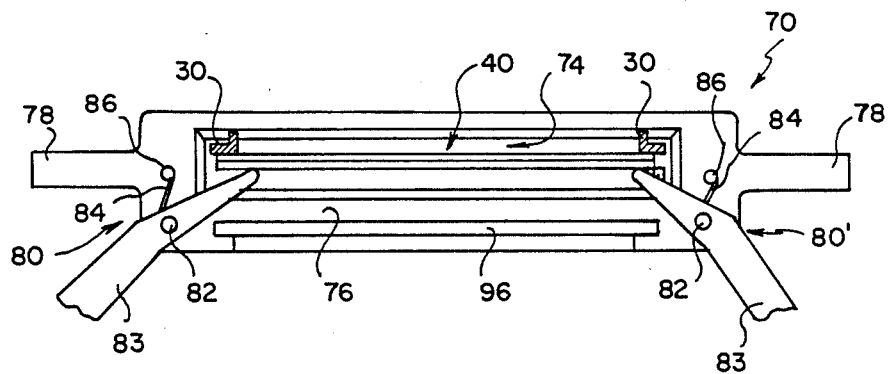
FIG. 6 is a sectional view taken along the line VI—VI of FIG. 5.

Although the supporting surface can be any suitable surface, preferably each of rails 29, 30 is a pair of rails, FIGS. 5 and 6, to provide the supporting surface for gel plate assembly 40. As is seen more clearly in FIGS. 5 and 7, the bottom of each rail features a supporting trough 32 with a front lip 34, that holds gel plate 40 from falling off the rails-see also FIG. 1. Trough 32 in turn comprises a vertical shoulder 36 and a bottom ledge 38. Further, each rail 29, 30 includes a flange 39 that extends the length of the rail, FIGS. 4, 7-8, and 10, to cooperate with clamps for the buffer tanks, as described hereinafter.

Each of the pairs of rails 29 or 30 is associated with its own clam shell. As such, the device permits two electrophoresis gel plate assemblies to be run simultaneously. Alternatively, additional pairs (not shown) can be mounted from the same post, the support being rotated about post 24 until the desired gel plate assembly is facing the operator.

Preferably, the gel plate supporting surfaces comprising the pair of rails is mounted to form an angle $\alpha$, FIG. 1, that is inclined from the vertical by an amount between about 5° and 10°. As such, the bottom of the gel plate and buffer tank 70 are closer to the operator, when the gel plate faces the operator, than are the top of the gel plate and buffer tank 100. The advantage is that, unlike perfectly vertical plate supports of conventional devices, no care is required to hold the plate on the support while clamps are mounted in place. Instead, the plate is simply inserted into troughs 32, and leaned back against rails 29 or 30. The troughs 32 are effective in preventing the plate from dropping lower, and angle $\alpha$ is effective in preventing plate 40 from tipping over, until buffer tanks 70 and 100 are installed.

Angle $\alpha$ is preferably no less than 5°, since otherwise the angle is insufficiently different from a vertical orientation, and tipping is more likely. It is preferably no greater than 10°, since more than that tends to make the device too bulky at the bottom.

Gel plate assembly 40, FIG. 3, is the entire assembly shown, which comprises a front plate 42, a rear plate 44, and spacers 46, 48 separating the two to allow gel (not shown) to be formed between them, as is conventional. Preferably, rear plate 44 is improved to insure superior formation and observance of dye lines in electrophoresed samples. That is, plate 44 comprises a front surface 50 and a rear surface 52. Rear surface 52 is preferably coated with a mirroring material 54, such as silver or aluminum, and a layer 56 is bonded over coating 54 to extend in back of the flow surface area of plate assembly 40. As used herein, the bonding of layer 56 "in back of the flow surface area" of the gel plate means, over an area having an extension that is coincident with, and behind, the flow surface area of the gel, wherein the electrophoresis lanes lie. This area is defined by length "l", FIG. 1, and width "w", FIG. 3. Layer 56 is selected from a material that is effective in distributing or transferring heat, for example, aluminum. This layer is tightly bonded to coating 54 over all of its surface, by using any suitable means, for example an adhesive such as an acrylic adhesive. The entire laminate is then overcoated with a non-conductive corrosion-resistant layer.

However, layer 56 is not used to dissipate heat from the gel plate. Rather, the supporting surfaces formed by rails 39 are deliberately held off from body 28 a distance effective to create a dead air space 58, FIGS. 4 and 8. This insulating air space insures that the heat generated by the process remains in place, thus reducing the time needed to achieve operating temperature.

Layer 56 is thus effective to transfer heat from the hotter center regions, to the peripheral regions, thereby reducing temperature gradients. As a result, dye lines form in the gel that have the desired straightness, and the results are free of thermally induced artifacts. The overall temperature, however, remains high, thus inducing the dye fronts to progress faster than is the case with water-backed units. That is, the water takes much longer to heat up to operating temperature.

The ability of the dye fronts to be processed substantially free of artifacts remains even when supplying as much as 60 watts of power to achieve temperatures as high as 70° C., when measured at the front of plate 42, producing dye front speeds as high as 0.5 cm/min.

Yet another advantage of such a gel plate is the mirrored surface. This surface insures that the user can more readily tell the condition of surface 50, FIG. 3. That is, the mirrored surface makes it easier to accurately introduce sample solution by pipette into the cavity between plates 42 and 44. It also helps reveal particles of dirt, if any, on surface 50 when plate 44 is being cleaned. The dye lines are also more easily detected with the mirror in place.

Preferably, one or both of the buffer tanks are removable and hence autoclavable. Most preferably, they are releasably mounted by clamping means that not only clamp the box in position, but also clamp the gel plate to the support.

Figure 7:
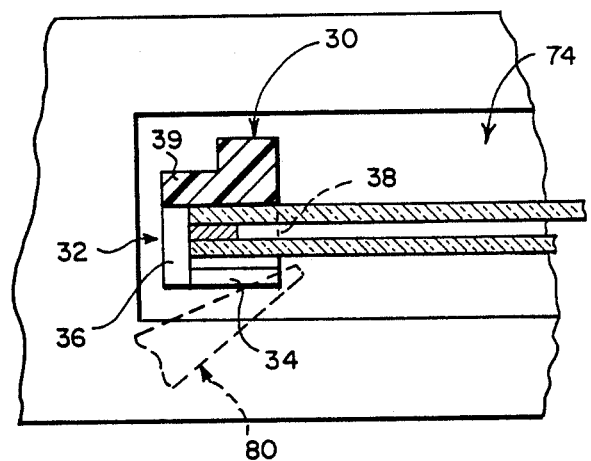
FIG. 7 is a fragmentary enlargement of the portion of FIG. 6 identified as "VII"

With respect to the bottom buffer tank 70, FIG. 4, such tank comprises a cavity 74, FIGS. 6 and 7 open at the top surface 76, FIG. 5. The tank has manual grasping ears 78 at either end, and two clamps 80, 80' journalled on post 82 to top surface 76. Each clamp has a handle portion 83. A torsion spring 84 is wrapped around post 82 at one end, FIG. 6, and secured at its other end to a screw 86 attached to surface 76. As a result, clamps 80 and 80' are biased to press inwardly-that is, clamp 80 is biased to rotate counterclockwise, FIG. 6, and 80' to rotate clockwise.

The effect is to not only clamp tank 70 to the support at rails 29, but preferably also to clamp gel plate assembly 40 between the buffer tank and the rails 29. By this construction, it is not necessary that separate clamps or fasteners by used to hold tank 70 in place, apart from those used to clamp the gel plate in place.

Clamps 80 and 80' work by simply grasping the clamp with the thumb and one of the ears with the fingers, and pressing against the torsion spring to release the clamp from contact with the gel plate. This in turn releases the buffer tank from engagement with rails 29 or 30, so that the buffer tank can be removed and cleaned.

As is conventional, a banana plug 90 is mounted at the side of tank 70 for connection to power wires. Inside the tank, plug 90 connects with a wire electrode 92, FIG. 5, that is supported by a rod or tube 94 that extends along the bottom of tank 70. Tube 94 and electrode 92 are preferably removable as a unit.

The front face 98 of tank 70 can be transparent, to aid in viewing the contents thereof.

Figure 8:
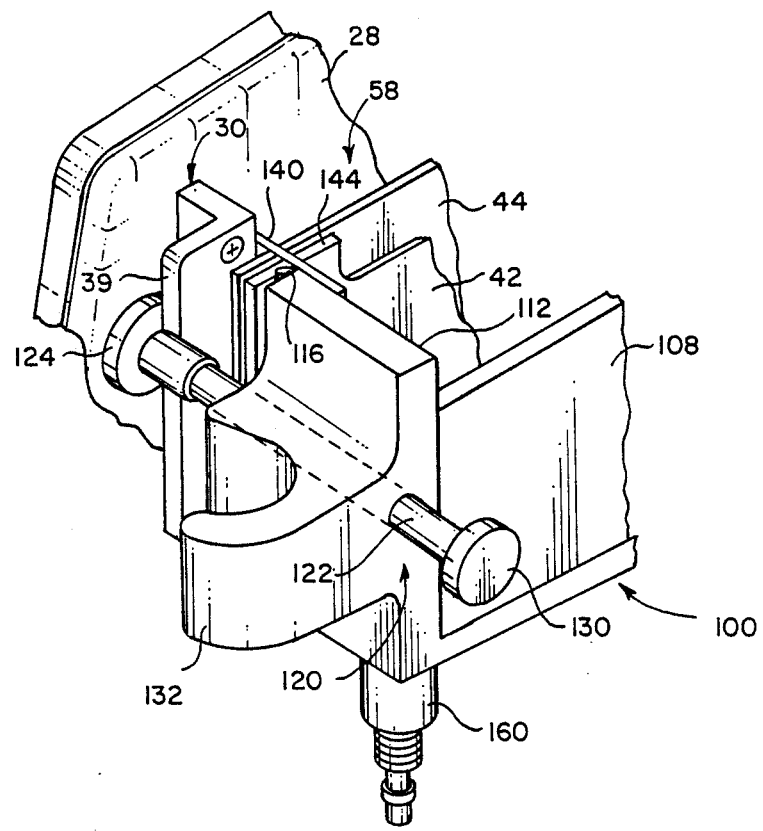
FIG. 8 is a fragmentary isometric view of the upper buffer tank in place in the device of the invention.
Figure 9:
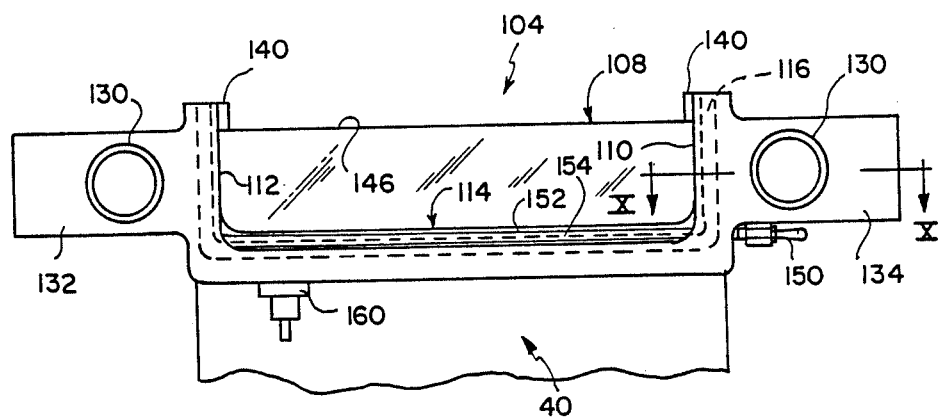
FIG. 9 is a front elevational view of the buffer tank of FIG. 8.
Figure 10:
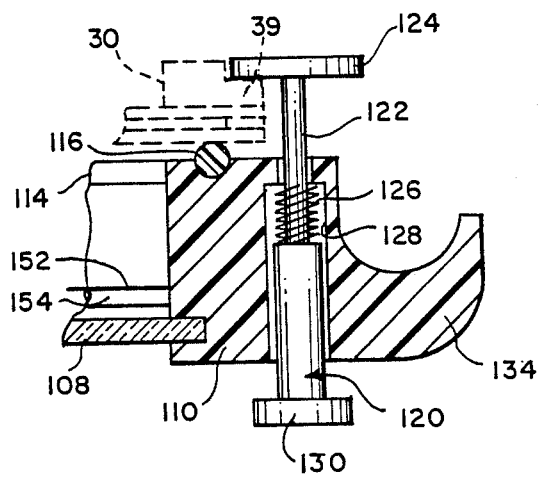
FIG. 10 is a fragmentary sectional view taken generally along the line of X—X of FIG. 9.

Similarly, tank 100 is releasably clamped to the other end of gel plate assembly 40, FIGS. 8–10. Tank 100 also comprises a cavity 104 defined by a bottom surface 106, FIGS. 8 and 10, a front transparent plate 108, FIGS. 8–10, side walls 110, 112, and a very short vertical back wall 114. Back wall 114 is shorter than the height of front plate 108, so that liquid in cavity 104 will contact gel plate assembly 40 (shown in phantom, FIG. 10) in contact with the tank 100. To insure the liquid does not pour out of cavity 104, a gasket 116 (shown in phantom in FIG. 9) traces a U-shape in a track along the back of sidewalls 110, 112 and back wall 114, FIGS. 9 and 10.

The clamps for tank 100 comprise a plunger 120, FIGS. 8 and 10, having a shaft 122 that extends through sidewall 110, to a disc 124 dimensioned to engage flange 39. Inside wall 110, shaft 122 is reduced in diameter, FIG. 10, to accommodate a compression spring 126 mounted within aperture 128 for the clamp. Button 130 is used to press the clamp against the bias of spring 126, thereby releasing the clamp, the buffer tank, and gel plate assembly 40 from engagement with rail 29 or 30. Griping ears 132, 134, FIGS. 8–10, are provided to assist in manually depressing plunger 120 and thus overcoming the bias of spring 126.

Any compression spring is useful for spring 126. Preferably, it is one providing a spring constant of about 0.735 N/mm, such as is achieved by two end-to-end springs P/N CO 480-045-2000 S manufactured by Associated Spring, Bristol, CT.

Other clamps can be used in place of the plungers 120. For example, pivoting clamps like those of bottom buffer tank 70, FIG. 4, could be mounted and biased to pivot about a vertical axis towards the back-side of rail 39. Similarly, the clamps of bottom buffer 70 could be replaced with the plungers 120 of the upper buffer tank, biased to press against gel plate assembly 40. Release in both cases would occur by pulling on the clamp mechanism. Because pushing is considered to be easier, the clamp arrangement actually shown is preferred.

A further improvement in tank 100 is the use of means that automatically position the tank at the top of gel plate 40. These comprise locators 140 that extend from trough 102 generally flush with top surface 142 of cavity 104, back beyond gasket 116. Locators 140 are essentially ears, constructed to ride on the top 144 of gel plate assembly 40, FIG. 8 (which top coincidentally coincides with the top surface 146 of front plate 108, FIG. 9).

By reason of this construction, any length gel plate assembly can be used in the device, without preventing tank 100 from being at the top of the assembly, provided the length is not greater than the length of rails 29 or 30. That is, tank 100 will always be located at the top of gel plate assembly 40, since locators 140 insure this.

Banana plug 150, wire 152 and supporting rod 154 are mounted in tank 100, in a manner similar to that of lower tank 70, FIGS. 9 and 10.

As is conventional, a drain valve 160 is mounted in bottom surface 106, FIGS. 8 and 9, for draining the tank.

Alternatively, not shown, plate 108 can be a magnifying plate to provide magnification.

The frame by which device 20 rotates comprises, FIG. 2, trapezoids 172 mounted vertically on two horizontal plates 174 and 176. Plate 174 is apertured at 178 to allow post 24 to freely extend through it. Plate 176 provides bushing 60, described hereafter. The outwardly facing edges 180, 182 of each trapezoid 172 provide the mounting support for the pairs of rails mounting on the clam shell bodies, shown in phantom. Bushing 60, FIG. 11, rides on point 184 of post 24. In this fashion, the entire frame comprising plate 174, 176, bushing 60, trapezoids 172 and the attached clam shell bodies and rails, rotates on post 24.

Figure 15:
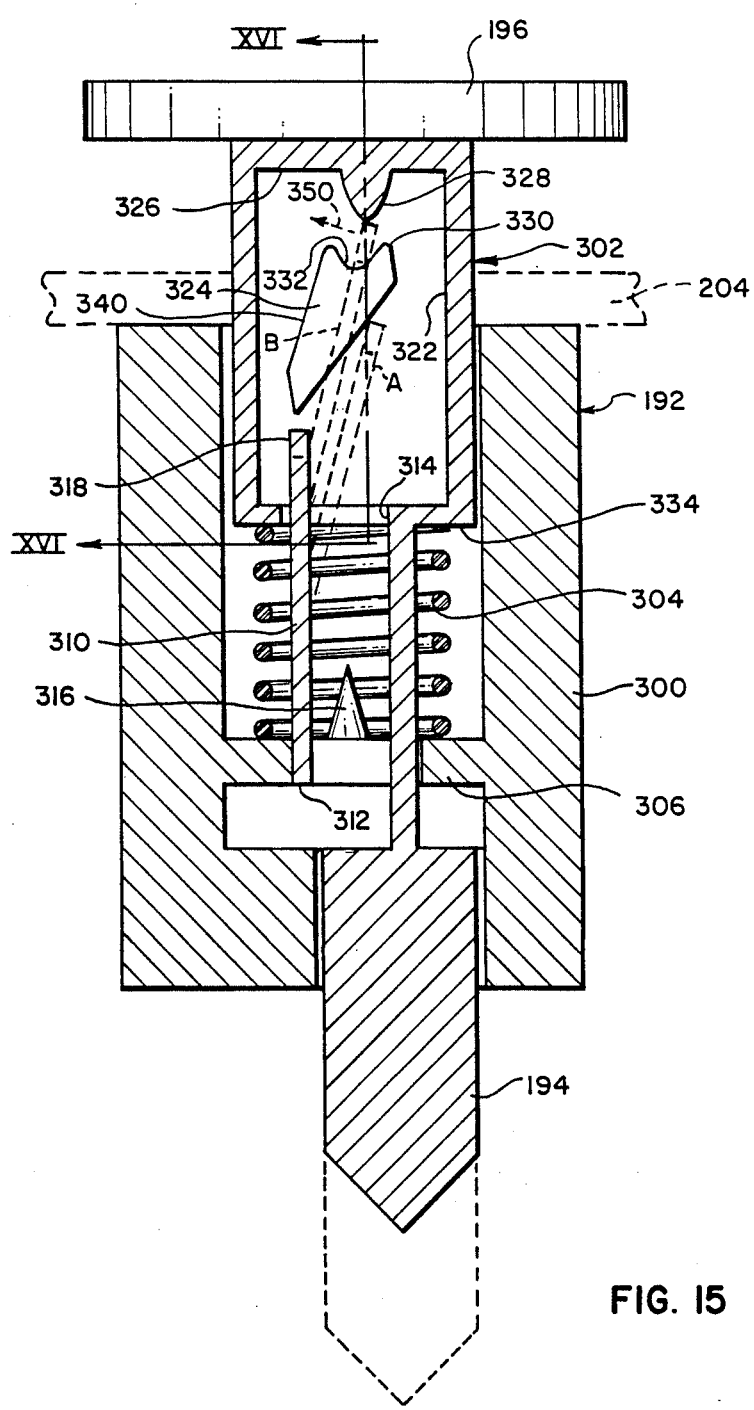
FIG. 15 is a vertical sectional view illustrating a preferred construction of the interior of the two-position latch.

In accordance with the invention, locking of the frame is provided by the locking mechanism 170, by which rotation of the device is temporarily restrained, FIGS. 2 and 11–18. Such a locking mechanism is useful for any device mounted for rotation, and is particularly suited for the electrophoresis device described above. Locking mechanism 170 preferably comprises, FIGS. 11–12, a lock plate 186 fixedly secured to post 24 and means on plate 176 of the frame for causing releasable engagement of the plate in one of two push positions. More specifically, plate 186 is provided about its circumference, which can be any shape but is preferably circular, with teeth 190, FIG. 12. Most preferably, the teeth are evenly spaced around the entire circumference. The releasable engaging means is constructed to engage plate 186 between any two adjacent teeth, either directly or indirectly. In the embodiment of FIGS. 11–12a and b, such engaging means provides direct engagement, as follows:

A conventional two-position latch 192 is provided, of the type commonly used with cabinet latches or ballpoint pens, shown in greater detail in FIG. 15. The working end of the latch comprises vertical member 194, that occupies one of two positions that alternate each time manual button 196 is pushed. In one position, shown in solid lines, FIG. 11, it is fully down and positioned between any two teeth 190. In the other position, member 194 is raised, shown in phantom, so as to be clear of teeth 190. Most preferably, teeth 190 are shaped so that outer edges 198 extend downwardly away from latch 192, being bent about a tooth radius 200 that is preferably centered between edges 198. Also, member 194 is preferably pointed at 202. By this construction, member 194 is not likely to "hang up" on the top of a tooth when the user pushes it down in a blind manner. Instead, point 202 of member 194 rides off a tooth 190 and into a space between the teeth. (Such spacing is designed to readily accommodate member 194.)

A grommet 204 is used to protect the interior of device 20 from liquid spills.

In such a construction, the user pushes button 196 once, and it and member 194 move down to the solid line position, FIG. 11, to lock device 20 against further rotation. Member 194 thus functions also as the means for engaging two adjacent teeth on the lock plate. When latch 192 is pushed again, button 196 and member 194 move up to the phantom position, which frees device 20 for endless rotation of the gel plate supports.

Alternatively, latch 192 can be constructed so that button 196 always stays up, and does not mirror the movement of member 194. However, such mirroring of the movement is preferred as a visual indication of whether the device is locked against rotation, or not.

Figure 14:
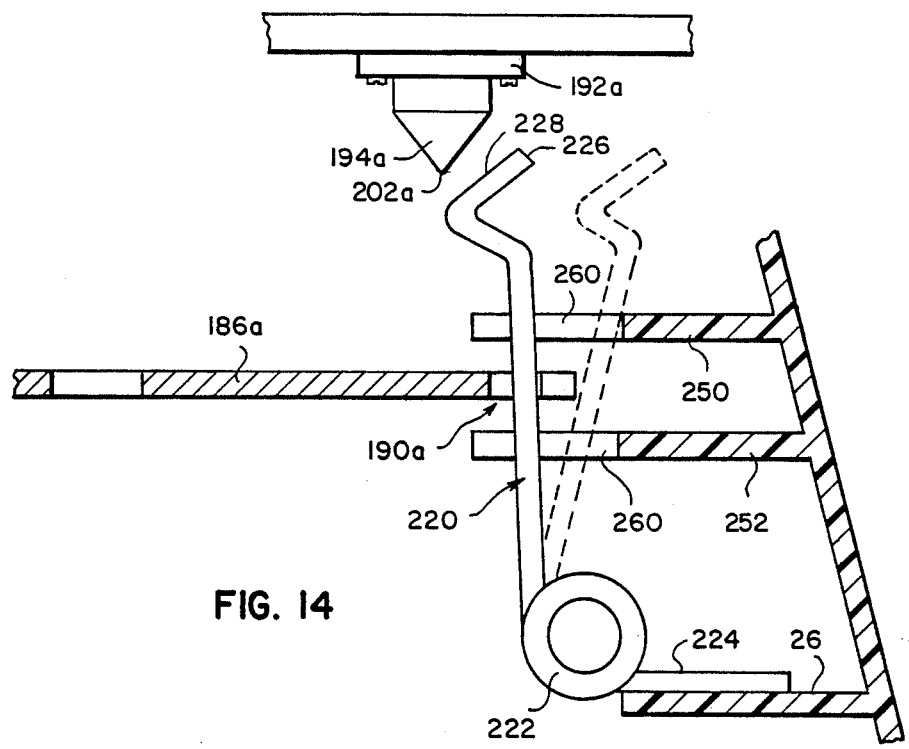
FIG. 14 is a fragmentary elevational view, partly in section, of the embodiment of FIG. 13.
Figure 13:
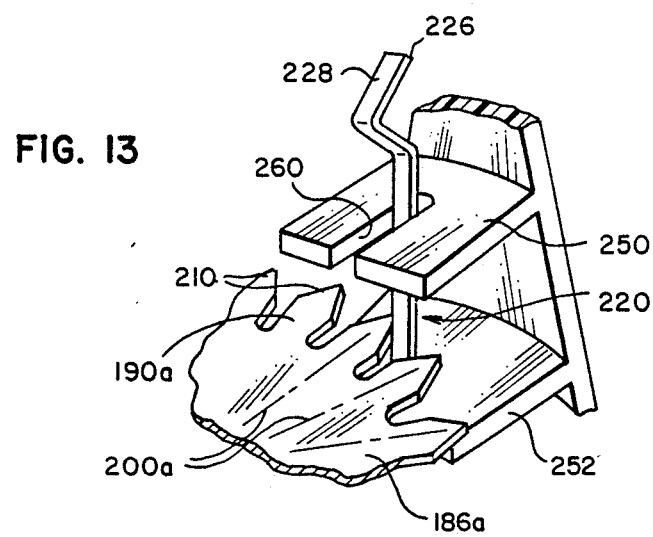
FIG. 13 is a fragmentary perspective view of an alternative embodiment of the locking mechanism.

In another embodiment, FIGS. 13 and 14, the engagement by the latch is indirect, and occurs when the manual button is raised, not lowered. Parts similar to those previously described bear the same reference numeral, to which the distinguishing suffix "a" is appended. Thus, latch 192a is as described in the previous embodiment, with member 194a having a point 202a. Lock plate 186a has circumferentially positioned teeth 190a, also as described previously. However, teeth 190a are preferably flat, with a point 210, FIG. 13, centered on a central radius 200a of each tooth 190a. The means that actually engage teeth 190a comprises a lever 220, biased to press against the teeth by reason of a torsion spring 222 of which lever 220 is an integral part, comprising one end of spring 222. (The opposite end 224 of spring 222 is secured to the gel plate support, e.g., a clam shell body 26, FIG. 14. Most preferably, end 226 of lever 220 is provided with a camming surface 228 shaped to cooperate with the shape of point 202a. Alternatively, point 202a can be replaced with a ridge, not shown, that provides a flat that mates with the flat on surface 228.

To ensure that lever 220 maintains an erect position for alignment with the space between adjacent teeth 190a, a pair of guide plates 250, 252 are provided, each with a slot 260 shaped to prevent lever 220 from being displaced sideways.

In use, lever 220 is biased to engage and lock plate 186a against rotation, shown in solid lines, FIG. 14, when member 194a is up. When latch 192a is pushed again, to occupy the "down" position, member 194a cams against lever 220 to deflect the latter to the position shown in phantom. This unlocks plate 186a and the device for endless rotation. When the button of latch 192a is pushed again, member 194a moves out of the way, allowing lever 220 to reengage the teeth. Because teeth 190a are pointed, lever 220 will not rest on a tooth but instead slips by any tooth that might be facing it, and moves into place between teeth. Alternatively, lever 220 can be rounded (not shown) about a vertical axis to further discourage lever 220 from resting on a tooth end.

Figure 16:
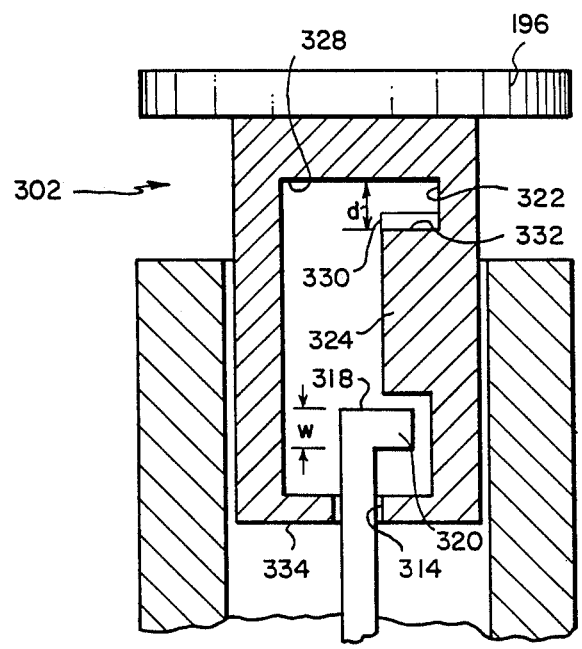
FIG. 16 is a sectional view taken along the line of XVI—XVI of FIG. 15.

A useful construction for the latch 192 or 192a is shown in FIGS. 15 and 16. More specifically, such latches 192 [here shown rectangular, but cylindrical shapes are useful] comprise a body 300 within which hollow actuator 302 freely reciprocates against a spring 304 anchored to an annular ring 306 inside body 300. A leaf spring 310 is anchored at one end 312 to ring 306 at the inside diameter of the ring. Ring 314 also supports a fixed stop 316. The opposite end 318 of leaf spring 310 projects through aperture 314 in actuator 302 and is provided with a finger 320, FIG. 16, that has a predetermined width "w". Actuator 302 has on its interior vertical wall surface 322 a camming projection 324 shaped as shown in FIG. 15. Top wall surface 326 of actuator 302 has a projection 328 that is spaced from camming projection a distance "d", FIG. 16, that exceeds width dimension "w" enough to permit finger 320 to slip into the space between wall projection 324, FIG. 15, and top surface projection 328. Upper surface 330 of projection 324, FIG. 15, has a cusp 332 that traps the finger when actuator 302 is released. Attached to bottom surface 334 of actuator 302 is member 194. Stop 316 keeps actuator 302 from moving down so far as to damage spring 310 or spring 304.

The actuation is as follows: when button 196 is depressed from its position shown in FIG. 15, against spring 304, actuator 302 is moved downwardly. Camming projection 324 moves against leaf spring 310 to force it to the right, FIG. 15, shown in phantom at "A". When finger 320 clears the top 330 of projection 324, it is forced into the space between projection 328 and projection 324. When button 302 is released, finger 320 falls into cusp 332, FIG. 15, as shown in the phantom position marked "B". (Leaf spring 310 does not, of course, move "up", but rather actuator 302 moves down. The phantom lines illustrate spring 310 in its relationship to the projections 328 and 324.) This engagement serves to keep button 196 in its "down" position. When next the button is pushed downward, the force of the leaf spring to the left, arrow 350, is sufficient to cause spring 310 to slip to the left of projection 324. When button 196 is released, spring 310 passes on the left side 340 of projection 324, thus allowing actuator 302 to return to the fully up position shown. In the meantime, member 194 moves down or up, between the two positions, as actuator 302 moves down or up.

Figure 17:
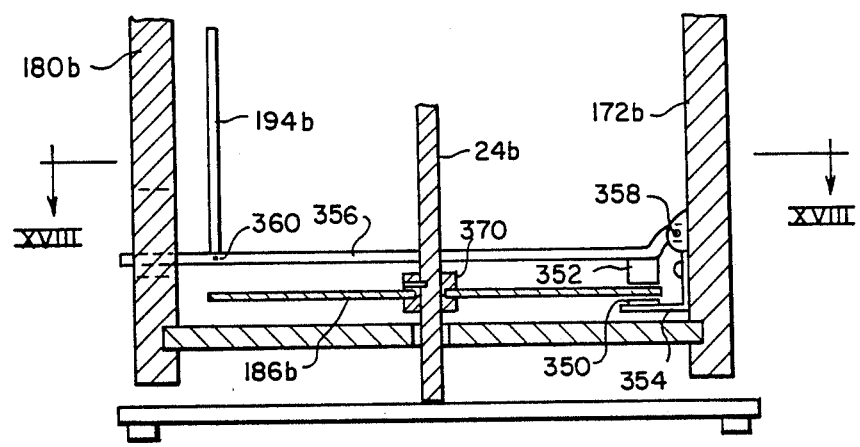
FIG. 17 is a fragmentary elevational view in section, similar to FIG. 11, illustrating yet another embodiment of the locking mechanism.
Figure 18:
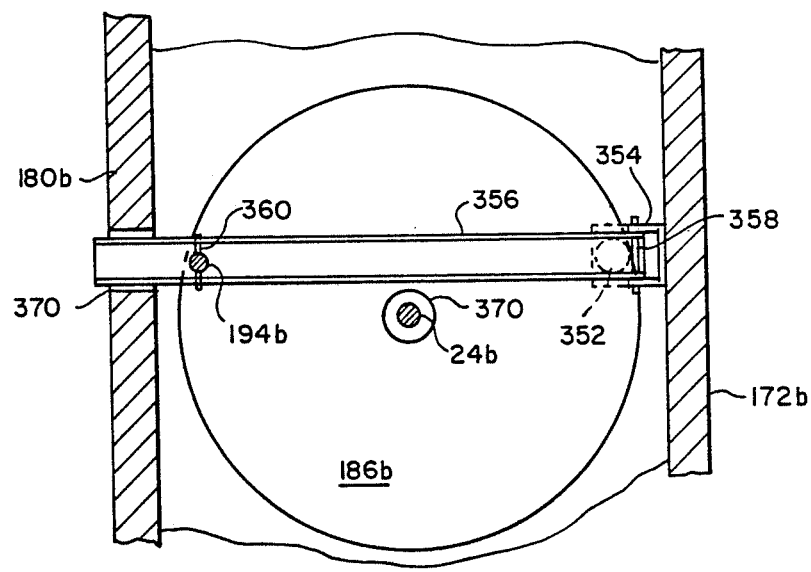
FIG. 18 is a sectional view taken generally along the line XVIII-XVIII of FIG. 17.

The locking mechanism need not be a lock plate with teeth that define a limited number of locking positions. It can alternatively be one that can lock in an infinite number of positions, as shown in FIGS. 17 and 18. Parts similar to those previously described bear the same reference numeral, to which the distinguishing suffix "b" is appended.

Thus, the two-position latch is identical to that described heretofore, except that member 194b is a push rod that extends from the latch, down to locking plate 186b that is secured to post 24b as before. In this case, however, plate 186b is a disk brake, such as a chromic anodized aluminum disk of conventional construction. Disk brake 186b is secured to post 24b by a collar 370. Associated with plate 186b are one and preferably two brake pads 350 and 352. Pad 350 is secured to an angle member 354 mounted on trapezoid 172b. Pad 352 is mounted on a lever arm 356 hinged at 358 to trapezoid 172b. Both pads are preferably a low compression set elastomer, such as rubber, also of conventional type.

To obtain sufficient locking power against inadvertent rotation of the device, member 194b is preferably attached by pin 360 at a location on lever arm 356 that gives a mechanical advantage of at least 5 to 1 to pad 352. As shown, the advantage is even more that that, for example, about 8 to 1.

To preclude lever arm 356 from bending due to torque loads incurred from the disk brake, arm 356 is mounted to move in a slot 370 in trapezoid 180b, FIG. 18.

In this embodiment, when the two-position latch is "down", the device is locked against rotation. As will be readily apparent, it can be locked with the device on trapezoids 172b and 180b positioned in any one of an infinite number of positions.

Alternatively (not shown), the latch member 194b can be pressed against lever arm 356, without being pinned thereto, a spring being provided to raise arm 356 and brake pad 352 off disk brake 186b, unless latch member 194b is depressed.

The invention has been described in detail with particular reference to preferred embodiments thereof, but it will be understood that variations and modifications can be effected within the spirit and scope of the invention.

What is claimed is:

1. In an electrophoresis device for electrophoretically separating charged compounds, the device comprising a support for mounting at least one gel plate assembly, a pair of buffer tanks for each gel plate assembly, means for mounting said pair of tanks at opposite ends of said each gel plate assembly, and means for applying a current at said opposite ends of said each plate assembly;
the improvement wherein said device further includes a base on which said support is mounted, means for rotating said support about said base about a generally vertical axis, and means for releasably locking said support in at least one position relative to said base.

2. A device as described in claim 1, wherein said base includes a vertically extending post coincident with said axis, and said support is pivotally mounted on said post.

3. A device as described in claim 2, wherein said releasable locking means comprises a lock plate secured to said post, said plate comprising a plurality of teeth radiating generally outwardly from the interior of the plate, centered on said post, and a two-position push latch on said support having a downwardly extending member, said member being latchable in two positions, said member in one of said positions being directly in contact with at least one tooth of said plate, and said member in the other of said positions being located out of contact with said plate, said latch being constructed to alternate between said two positions each time it is pushed.

4. A device as described in claim 3, wherein said teeth are crimped about a horizontal radius centered in each of said teeth, the edges of said teeth being shaped to extend away from said latch, whereby said member when contacting said teeth is encouraged to occupy a space between two adjacent teeth.

5. A device as described in claim 2, wherein said releasable locking means comprises a lock plate secured to said post, said plate comprising a plurality of teeth radiating generally outwardly from the interior of the plate, centered on said post, means for engaging said plate between any two adjacent ones of said teeth, means for biasing said engaging means into engagement between said two teeth, and a two-position push latch on said support having a downwardly extending member, said member being latchable in two positions, said member in one of said positions being in contact with said engaging means and in the other of said two positions, out of contact with said engaging means, said engaging means and said member being provided with mutually engaging camming surfaces effective to force said engaging means against said biasing means and out of engagement with said teeth.

6. A device as described in claim 1, wherein said releasable locking means comprise a lock plate secured to said base, said plate comprising a plurality of teeth extending around the circumference of said plate, and means on said support for engaging said plate between any two adjacent teeth, said engaging means being directly or indirectly activatable by a two-position push latch on said support having a downwardly extending member, said member being latchable in two positions, one of said positions being effective to place said engaging means between said two teeth, and the other of said positions being effective to remove said engaging means from all of said teeth of said lock plate.

7. A device as defined in claim 1, wherein said locking means comprise a disk brake secured to said base, and means on said support for engaging said brake, said engaging means including at least one brake pad, and further including a two-position push latch on said support having a downwardly extending member that is latchable in two positions, said engaging means being activatable by said latch member on said support, one of said positions of said latch member being effective to push said brake pad against said disk brake, and the other of said positions being effective to remove said pad from said disk brake.

8. A device as defined in claim 7, wherein said engaging means further includes a lever arm to which said brake pad is attached, said member of said latch being attached to said lever arm at a position providing a mechanical advantage to said pad of at least 5 to 1.

* * * * *

UNITED STATES PATENT AND TRADEMARK OFFICE
CERTIFICATE OF CORRECTION

PATENT NO. : 4,800,010
DATED : January 24, 1989
INVENTOR(S) : Hellman, Jr., Robert R.

It is certified that error appears in the above-identified patent and that said Letters Patent is hereby corrected as shown below:

Col. 2, lines 44-45 should read:
--Fig. 7 is a fragmentary enlargement of a portion of Fig. 6;--

Col. 3, lines 54-55, the sentence at those lines should read:
--Further, each rail includes a flange 39 that extends the length of the rail, as shown for rail 30 in Figs. 8 & 10,--

Col. 4, line 43, should read:
--flanges 39 are deliberately held off from body 28 a distance--

Col. 5, line 6 should read:
--clamp the tank in position, but also clamp the gel plate to--

Col. 5, line 23 should read:
--fasteners be used to hold tank 70 in place, apart from--

Col. 5, line 38 should read:
--The front face 96 of tank 70 can be transparent, to aid--

Col. 5, line 47 should read:
--gel plate assembly 40 (shown unnumbered in phantom, Fig. 10) in--

Col. 6, line 14 should read:
--trough 102 generally flush with top surface 146 of cav- --

Signed and Sealed this

Seventeenth Day of April, 1990

Attest:

HARRY F. MANBECK, JR.

*Attesting Officer*  *Commissioner of Patents and Trademarks*